United States Patent [19]

Schreck et al.

[11] Patent Number: 5,683,979
[45] Date of Patent: Nov. 4, 1997

[54] MALODOR COUNTERACTANT COMPOSITION AND PROCESS FOR USING SAME

[75] Inventors: Lisa Schreck, Tinton Falls; Mary E. Gordon, Belford; Marie R. Hanna, Keyport; Ruth M. Sutcliffe; William L. Hamilton, both of Middletown, all of N.J.

[73] Assignee: International Flavors & Fragrances Inc., New York, N.Y.

[21] Appl. No.: 647,243

[22] Filed: May 9, 1996

Related U.S. Application Data

[60] Provisional application No. 60/008979, Dec. 21, 1995.
[51] Int. Cl.⁶ ............................................. A61K 7/46
[52] U.S. Cl. ............................................. 512/13; 424/76.4
[58] Field of Search ............................... 512/13; 424/76.4

[56] References Cited

U.S. PATENT DOCUMENTS

| 4,840,792 | 6/1989 | Joulain et al. | 512/17 |
| 5,354,737 | 10/1994 | Barr et al. | 512/17 |
| 5,380,707 | 1/1995 | Barr et al. | 512/17 |

FOREIGN PATENT DOCUMENTS

| 7-227308 | 8/1995 | Japan | 512/17 |

OTHER PUBLICATIONS

International Product Alut, vol. 5 #10 (1992).

*Primary Examiner*—James H. Reamer
*Attorney, Agent, or Firm*—Arthur L. Liberman

[57] ABSTRACT

Described is a process for counteracting malodors including but not limited to pet malodor, tobacco malodor and mildew malodor comprising using as an additive to a base perfume composition a mixture consisting essentially of from about 20 up to about 60% musk, from about 30% up to about 70% citrus, and from about 1% up to about 20% mint. Adding from about 0.5% up to about 20% of such a malodor coverage formulation will yield from about a 10% up to about a 75% improvement in malodor neutralization efficacy; and a composition useful in such process.

3 Claims, 2 Drawing Sheets

MALODOR COUNTERACTANT COMPOSITION AND PROCESS FOR USING SAME

RELATED COPENDING PATENT APPLICATIONS

This application is a continuation-in-part of Provisional Specification 60/008979 filed on Dec. 21, 1995 entitled: "MALODOR COUNTERACTANT COMPOSITION AND PROCESS FOR USING SAME". Benefit of said specification 60/008979 is hereby claimed under 35USC§119 (e).

BACKGROUND OF THE INVENTION

Our invention covers technology for the creation and quantitative performance testing of fragrances that have enhanced malodor neutralizing capacity. This technology is focused on selected malodors important to household products. An array of malodor types that can be covered include but are not limited to urine and fecal odors; cooking odors such as chicken, seafood and garbage; pet odors; hair dye and smoking tobacco odors in addition to mildew and wet basement odors. Accordingly, our formulation can be used in a wide variety of applications such as air and carpet freshening products and upholstery and hard surface cleaners.

The prior art contains a number of attempts at malodor coverage. The malodor coverage achieved by our invention is unobvious, unexpected and advantageous over the prior art which is set forth below.

Thus, Barr, et al I, U.S. Pat. No. 5,354,737 issued on Oct. 11, 1994 discloses a fragrance composition said to have enhanced efficacy for masking malodor for extended periods of time, the fragrance composition containing fragrance materials that provide a topnote and/or a middle note and/or a bottom note and also containing more than 28% and up to 95% by weight of the total weight of the composition of acetyl hexamethyl tetralin. Barr, et al states that the fragrance composition can be incorporated in deodorant compositions to be applied to a person's skin, e.g., in axillary regions, to combat body malodor including malodor arising in axillary regions. A similar disclosure is set forth in U.S. Pat. No. 5,380,707 issued on Jan. 10, 1995 (Barr, et al II).

Pola Chem Industries, Japan Published Application No. JP 7133490 discloses a long-lasting deodorant with malodor masking effect comprising a perfume composition containing, for example, carvone, pulegone, menthol, menthone, cineole, camphor and methyl salicylate and is abstracted in *DERWENT CHEMICAL PATENTS INDEX ALERTING ABSTRACTS BULLETIN*, COUNTRY ORDER, Week 9530, issued Aug. 25, 1995 as follows:

\*POKK D22 95-227308/30 \*JP 7133490-A Long lasting deodorant with malodour masking effect-comprises perfume, compsn. contg. e.g. carvone, pulegone, menthol, menthone, cineole, camphor and methyl salicylate
POLA CHEM IND INC 93.11.10 93JP-305850
E19 P34 (D23) (C11B9/00, A61K 7/46, A61L9/01)

Deodorant contains 10–90 (pref. 30–60), wt. % of a perfume compsn. consisting of at least one of carvone of formula (I), pulegone of formula (II), menthone of formula (III), menthol of formula (IV), borneol of formula (V), camphor of formula (VI), cineole of formula (VII), methyl salicylate of formula (VIII), thymol of formula (IX), carvacrol of formula (X), bornyl acetate of formula (XI), anethole of formula (XII), and camphene of formula (XIII).

ADVANTAGE - The deodorant has good malodour masking effect for a long periods. Also, the compsn. has sensorial deodorising effect. (7pp Dwg.No.0/0) C95-125013

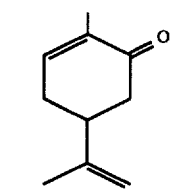 (I)

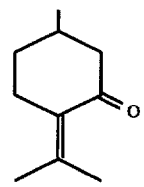 (II)

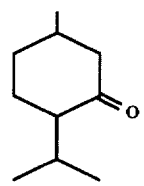 (III)

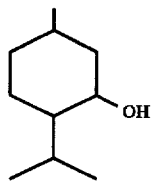 (IV)

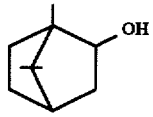 (V)

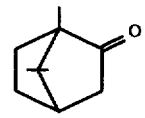 (VI)

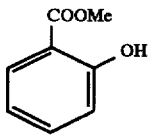 (VIII)

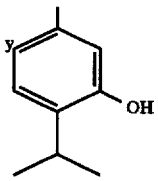 (IX)

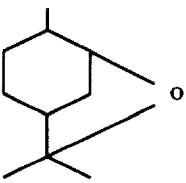 (VII)

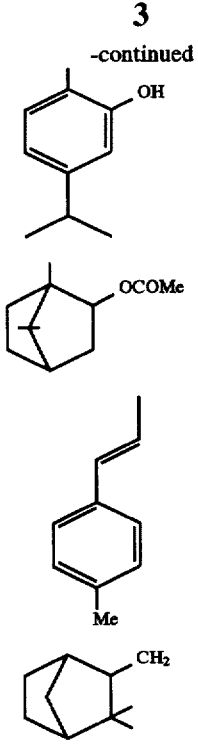

(X)

(XI)

(XII)

(XIII)

Pola Chem Industries Inc., Japanese Published Application No. JP 103964, covering selection of masking perfume based on theorization of masking by representing odorant for masking and similar odorant in making perfume separately as vectors and selective perfume(s) as indexes is abstracted as follows:

*POKK D21 95-188003/25 *JP 7103964-A Selection of masking perfume, based on theorization of masking - by representing odorant for masking and similar odorant in making perfume separately as vectors and selective perfume (s) as indexes

POLA CHEM IND INC 93.10.04 93JP-248350
S03 (D13) (95.04.21) G01N 33/00, A61K7/46

New selection comprises representing as odorant to be masked and an odorant similar to the odorant to be masked in a masking perfume separately as vectors and selecting a suitable perfume(s) with the similarity and the ratio of the magnitude of the two vectors as indexes.

ADVANTAGE - The method permits easy selection of appropriate masking perfumes to facilitate prepn. of cosmetic materials and processed foods. (10pp Dwg. No. 0/0) C95-087215

Toppan Printing Company Limited, Japanese Published Application No. JP 7136239, discloses a deodorant containing benzoquinone derivatives in ultra small amounts for deodorizing malodors such as mercaptans and is abstracted in DERWENT CHEMICAL PATENTS INDEX ALERTING ABSTRACTS BULLETIN, COUNTRY ORDER, Week 9530, issued Aug. 25, 1995 as follows:

*TOPP D22 95-227448/30 *JP 7136239-A Deordant contg. benzoquinone deriv. - in ultra small amt. for deodorising e.g. mercaptan, for utilisation in various forms TOPPAN PRINTING CO LTD 93.09.24 93JP-237685
E14 P34 (95.05.30) A61L9/01
93.12.14 93JP-313113
Addnl.Data: DAINIPPON JOCHUGIKU KK (DAAE)

Deodorant contains benzoquinone deriv(s). of formula (1), R1, R2 and R3=H, 1–4 C lower alkyl, 1–3 C lower alkoxy, halo or trifluoromethyl, provided at least one is not H.

ADVANTAGE - The deodorants exert high detergency against various bad-smelling odorant, including mercaptans, in a very small amt. and allows use in various forms. (4 pp Dwg.No.0.0) C95-104573

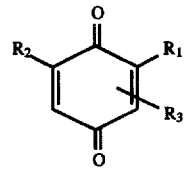

Joulain, et al, U.S. Pat. No. 4,840,792 issued on Jun. 20, 1989, entitled "AGENT NEUTRALIZING BAD SMELLS FROM EXCRETIONS AND EXCREMENTS OF ANIMALS", discloses and claims "a method for neutralizing disagreeable odours from animal excretions and excrement, comprising the steps of applying to a surface having a significant odour from animal excretions or excrement an agent including a compound selected from the group consisting of $C_{10}$ to $C_{12}$ aliphatic alcohols, $C_{10}$ to $C_{13}$ aldehydes, $C_{13}$ to $C_{18}$ aliphatic ketones, aromatic ketones having a musk odour and up to 18 carbon atoms, $C_8$ to $C_{15}$ aliphatic esters, methyl anthranilate, methyl N-methylanthranilate, p-cresyl phenylacetate, amyl salicylate, coumarin, dihydrocoumarin, gammadecalactone, dodecalactone, undecalactone, eugenol, isoeugenol, diphenyl oxide, the methyl and ethyl ethers of naphthol, galaxolide, indole and its reaction products with hydroxycitronella, tridecene-2-nitrile, and 2-(2'-methylpent-2'enyl)-5-methyl pyridine, in an amount effective to neutralize disagreeable odors from said excretions or excrement, said agent having a vapour tension of less than or equal to 4Pa at 25° C."

Hoechst Belgium Patent No. 1007195 also discloses malodor coverage and is abstracted at DERWENT CHEMICAL PATENTS INDEX ALERTING ABSTRACTS BULLETIN, COUNTRY ORDER, Week 9525, issued Jul. 21, 1995 as follows:

FARH D15 95-016323/03 =BE 1007195-A3 Sewage plant odour redn. - by adding acidic aq. glyoxal soln. into aq. effluent passing from sedimentation tanks to consolidation tanks SOC FR HOECHST 93.06.03 93FR-00663
E17 (95.04.18) *GB 2279070-A C02F
94.06.02 94BE-000554

Unpleasant odours in sewage plants are reduced by introducing an aq. soln. of glyoxal, having pH below 3, into a stream of aq. effluent passing from sedimentation tanks to consolidation tanks in the plant.

Pref., 1–24, esp. 1.9–3.3, moles glyoxal are used per mole $H_2S$ in the aq. effluent.

ADVANTAGE - Process reduces olfactory pollution, water pollution near the plant and Thiotrix bacterial proliferation.

Nothing in the prior art discloses the unobvious, unexpected and advantageous malodor coverage results that we have achieved as a result of the use of our formulation containing from about 20 up to about 60% (by weight) of a musk; from about 30 up to about 70% by weight of a citrus aroma; and from about 1 up to about 20% by weight of a mint aroma.

THE INVENTION

Our invention is directed to a malodor counteractant composition and a process of using same.

Our malodor composition neutralizes the following malodors, inter alia:

pet (cat urine);
human urine;
human fecal;
smoking tobacco;
cooking (seafood);
cooking (onion);
cooking (fried chicken);
garbage; and
mildew.

The malodor maskant composition of our invention contains from about 20% up to about 60% of a musk note; from about 30% up to about 70% of a citrus note; and from about 1% up to about 20% of a mint note.

The malodor maskant composition of our invention is intended to be used at levels of from about 0.5% by weight up to about 20% by weight based on the total quantity of composition containing fragrance and maskant.

The final fragrance maskant composition is intended to be incorporated into consumer products (e.g. air, carpet and upholstery fresheners) at levels of from about 0.6% up to about 25% by weight of the consumer product.

The musk note can be any one of a number of musks such as GALAXOLIDE® (registered trademark of International Flavors & Fragrances Inc. of New York, N.Y.), pentadecanolide, EXALTOLIDE® (trademark of Firmenich, et cie of Geneva, Switzerland), and the like.

The citrus notes can be citral, lemon oil, orange oil, geranylnitrile, citronellol, and the like.

The mint notes can be menthone, menthol, corn mint oil and the like.

Preferably, the musk note is GALAXOLIDE®. The preferred citrus note is citral refined; and the preferred mint note is corn mint oil.

Figure 1:
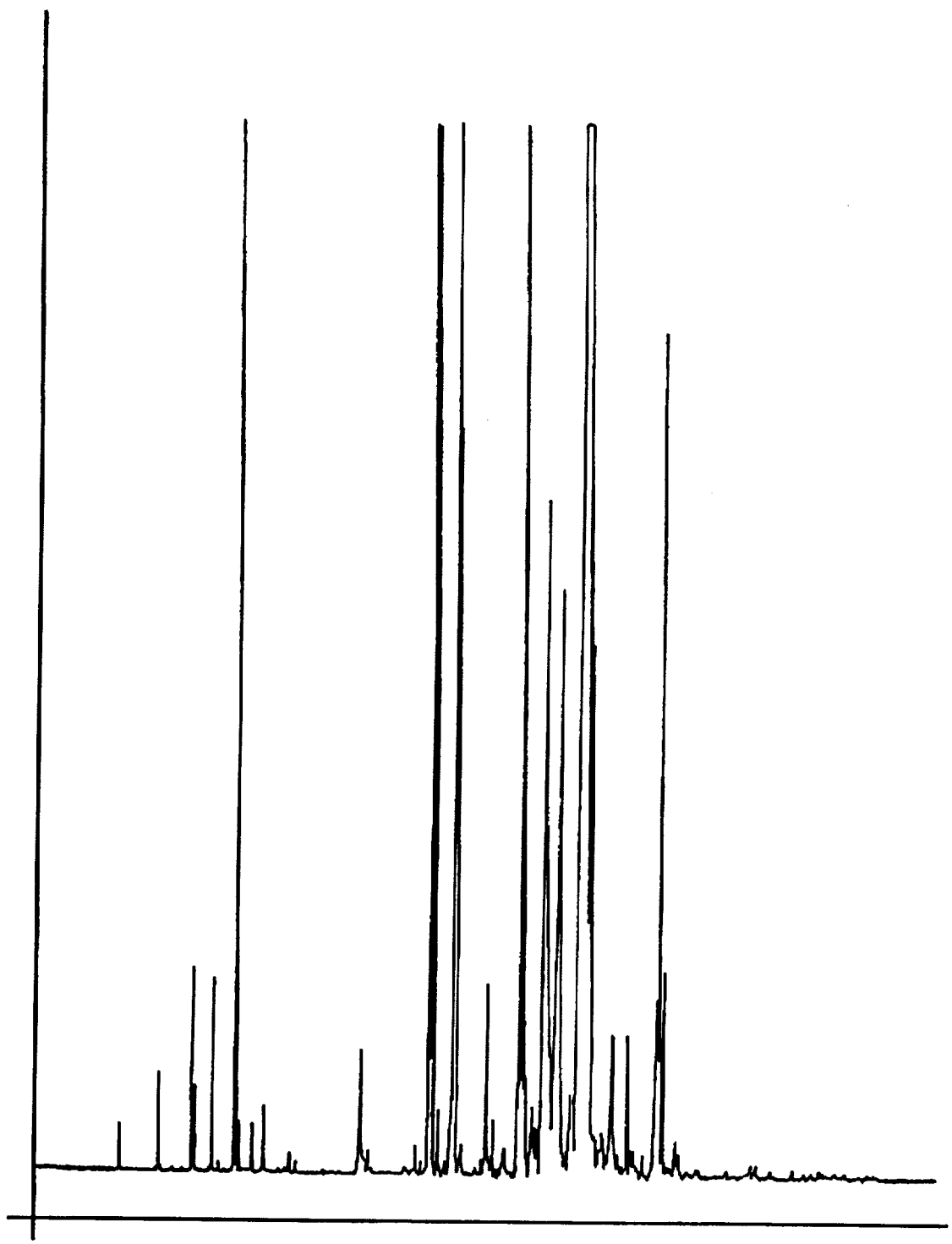
FIG. 1 is a GLC profile for the corn mint oil used in the preferred embodiment of our invention (Conditions: 15 meter carbowax-20M column programmed from 70°–220° C. at 4° C. per minute).
Figure 2:
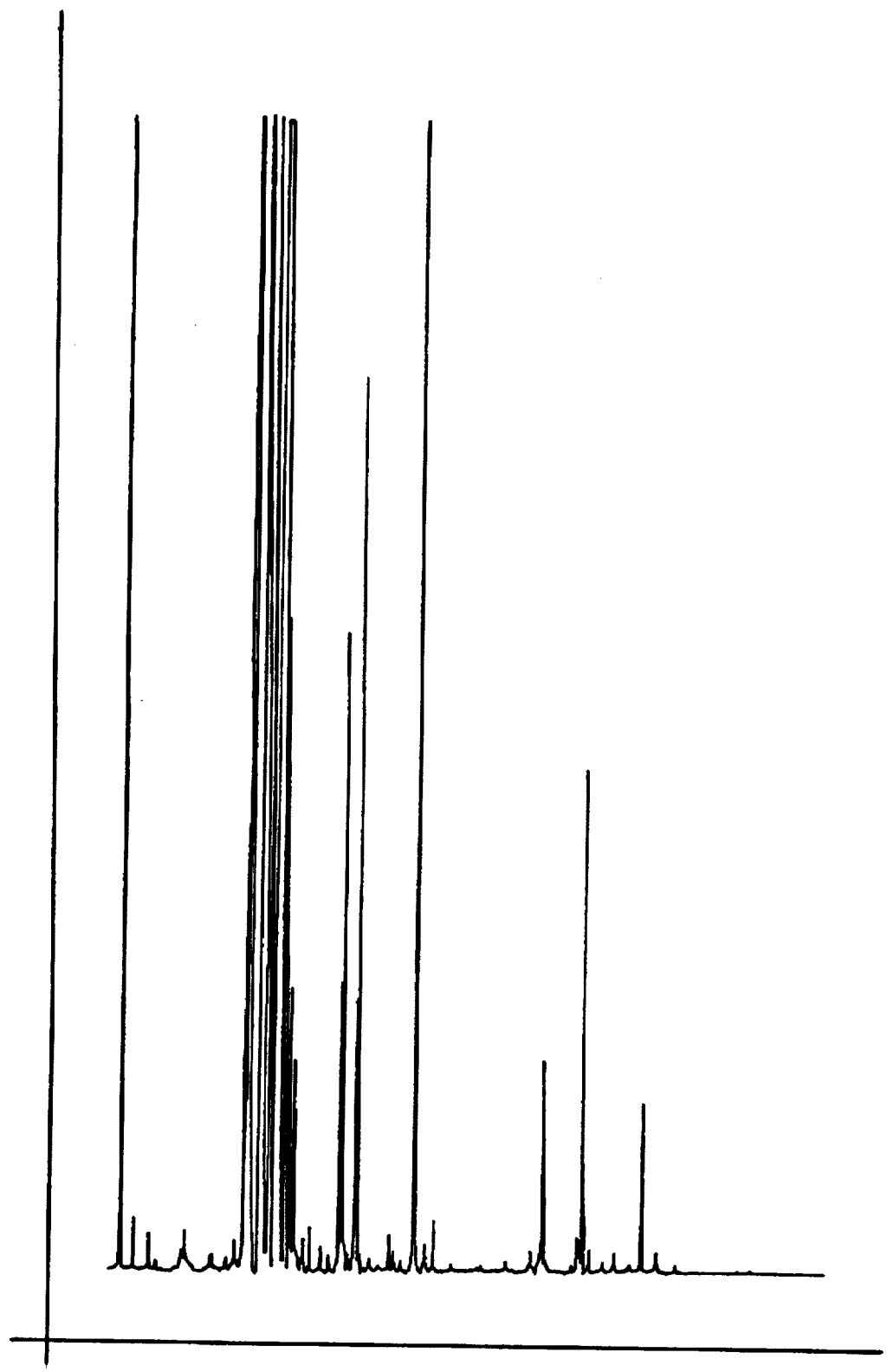
FIG. 2 is another GLC profile of the corn mint oil used in the preferred embodiment of our invention (Conditions: 50 meter OV1, dual fused silica system programmed from 70°–220° C. at 4° C. per minute).

The corn mint oil is defined according to FIGS. 1 and 2.

The most preferred embodiment is:

40% GALAXOLIDE®;
50% citral refined; and
10% corn mint oil.

Malodor neutralization is evaluated by placing a specified amount of malodor into an uncapped, 1 ounce wide-mouth jar. This jar is placed into an 8 ounce wide-mouth jar containing a specified amount of test material or finished fragrance. The quantities of malodor and fragrance are dependent on the specific malodor model used. The 8 ounce jar is capped and allowed to equilibrate. The panelists then rate the headspace for (1) total intensity, (2) malodor intensity, (3) overall like/dislike (hedonics). They are provided with an identified sample of malodor as a reference. Each group of samples presented to the panel contains an unidentified positive control (a fragrance material with no malodor), two unidentified negative controls (malodor with no fragrance) and up to twelve test samples (each fragrance is presented in duplicate or triplicate).

It is to be noted that evaluations are carried out by 18–24 panelists who have been extensively screened for their olfactory acuity and trained in the method of evaluation, Magnitude Estimation. Magnitude estimation of odor intensities provides normally distributed data that can be analyzed by parametric statistical techniques. For information on Magnitude Estimation, see ASTM Document #E1697-95, Standard Test Method for Unipolar Magnitude Estimation of Sensory Attributes, available from ASTM, 100 Barr Harbor Drive, West Conshohocken, Pa. 19428-2959. Panelist performance is constantly monitored and reviewed.

All samples are coded with random 5-digit numbers. Panelists are instructed to select samples from the test set and evaluate them in a random order.

The results of these experiments are expressed in terms of malodor reduction (neutralization), change in overall intensity and improvement in hedonics. The percent malodor reduction is calculated as:

% Neutralization=100×[1-(malodor intensity/total intensity)].

The positive control is normally rated as providing approximately a 95% malodor neutralization; the negative control is less than 10%.

One of the important attributes of the formulations of our invention is that their efficacy should not be achieved by "overpowering" the malodor but by "blending" with it. In order to substantiate this attribute, the total intensity of the "fragrance+malodor" sample cannot be statistically more intense than the "malodor" sample alone. Also, there must be a statistically significant improvement in the perceived pleasantness (hedonics). Regarding the foregoing, reference is herewith made to Example C, infra.

The technology which we have developed as exemplified below and as set forth, supra, is based upon a fragrance composition's ability to blend with a specific malodor in such a fashion as to be quantified and documented. In addition to having the appropriate aesthetic appeal, these fragrances must also meet the following technical criteria:

1. significant reduction in perceived malodor when compared to appropriate control fragrances;
2. no significant increase in overall intensity when the fragrance is combined with malodor; and
3. significant increase in the level of perceived pleasantness.

The following examples are intended to indicate how the invention is to be practiced, but the invention is not to be limited thereto and is only to be limited to the claims as set forth, infra.

EXAMPLE 1

EXAMPLE FRAGRANCE A: The following floral aldehydic fragrance was prepared.

| Ingredients | Reference Note | Parts |
|---|---|---|
| Amyl Cinn Ald Coeur | 1 | 0.0157 |
| Benz Sal | 2 | 0.0714 |
| Cinn Alc | 3 | 0.0143 |
| CYCLACET® | 4 | 0.0071 |
| CYCLAPROP® | 5 | 0.0071 |
| Dihydro Myrcenol | — | 0.0143 |
| Dihydro Terpineol | — | 0.0714 |
| Dipropylene Glycol | — | 0.0957 |
| GALAXOLIDE® Dep 50 Pct | 6 | 0.1429 |
| Hexyl Cinn Ald | 7 | 0.1986 |
| Lilial® | 8 | 0.1486 |
| Lyral® | 9 | 0.0229 |
| Meth Ionone Gamma A | 10 | 0.0286 |
| Phen Eth Acet | 11 | 0.0286 |
| Phen Eth Alc White Extra | 12 | 0.1000 |
| Tonalid® | 13 | 0.0214 |
| Trimofix "O"® | 14 | 0.0071 |

REFERENCE NOTES FOR FRAGRANCE A

1. ∝ Amyl Cinnamic Aldehyde
2. Benzyl Salicylate
3. Cinnamyl alcohol
4. Hexahydro-4,7-methanoinden-5-yl acetate
5. Hexahydro-4,7-methanoinden-5-yl prepionate
6. Structures on page 14 infra
7. ∝ Hexylcinnamic Aldehyde
8. p-t-butyl-∝methyl-dihydro cinnamic aldehyde
9. (4-hydroxy-4-methylpentyl)-3-cyclohexene-1-carboxaldehyde
10. Gamma methyl ionone
11. β-Phenyl Ethyl acetate
12. β-Phenyl Ethyl alcohol
13. 6-acetyl-1,2,3,4-tetrahydro-1,1,2,4,4,7-hexamethyl naphthalene
14. Methyl-2,6,10-trimethyl-2,5,9-cyclododecatrien-1-yl Ketone This fragrance is used in the following Examples:

| | Malodor Neutralization Test Results (a) | | |
|---|---|---|---|
| FRAGRANCE | % Malodor Neutralization (b) | % Chance in Overall Intensity (a) | % Improvement in Hedonic (d) |
| A | 42% | 14% | 27% | a. Results are based on the average of two independent samples, each evaluated by 18–24 panelists.
b. % Neutralization + 100 × [1-malodor intensity/total intensity].
c. Percent difference between the overall intensity of the malodor sample and that of the fragranced sample. Negative numbers indicate an overall reduction in intensity. Those differences which are statistically significant ($p < 0.05$, one-tailed t statistic) are indicated by "*".
d. Percent difference between the hedonic rating of the pure malodor sample and that of the fragranced sample. A 100% reduction would be the neutral point on the scale. Those differences which are statistically significant ([<0.05, one-tailed statistic) are indicated by "*".

The evaluations were carried out according to the procedure set forth on page 9 lines 9–38 supra. The malodor used in the example is a synthetic cat urine composed of ingredients determined by NMR, IR and Mass Spectral analysis to be present in natural cat urine.

The following malodor maskant formulation is prepared and called the NEUTRIFF® formulation (trademark of International Flavors & Fragrances Inc.):

EXAMPLE NEUTRIFF® FORMULATION

40% GALAXOLIDE® (50% solution in diethylphthalate);
50% Citral refined;
10% Corn mint oil (having a GLC profile as set forth in FIGS. 1 and 2).

This NEUTRIFF® formulation is used in the following examples:

The following table sets forth the increase in percent pet malodor coverage as a result of adding the NEUTRIFF® formulation described above to the fragrance described above in a 90:10 ratio (Fragrance:NEUTRIFF®).

The evaluations were carried out according to the procedure set forth on page 9 lines 9–38 supra. The malodor used in the example is a synthetic cat urine composed of ingredients determined by NMR, IR and Mass Spectral analysis to be present in natural cat urine.

In the following Example, the "expected percent malodor coverage equals (concentration of original fragrance × percent malodor neutralization provided by the original fragrance) plus (concentration of NEUTRIFF® formulation × percent malodor neutralization provided by the NEUTRIFF®).

| | NEUTRIFF® DATA | | | | |
|---|---|---|---|---|---|
| Fragrance ID | % Pet Malodor Neutralization by Fragrance without NEUTRIFF® (a) | % Pet Malodor neutrtalization NEUTRIFF® Alone (a) | Expected % Pet Malodor Neutralization of Combination of Fragrance with NEUTRIFF®(b) | Actual % Pet Malodor Neutralization of Combination of Fragrance with NEUTRIFF® (a) | % Increase in Pet Malodor Neutralization (c) |
| A | 42 | 88 | 47 | 81 | 72 | a. % Neutralization = 100 × [1-malodor intensity/total intensity].
b. Expected % Neutralization = (concentration of original fragrance × % neutralization provided by the original fragrance) + (concentration of NEUTRIFF® × % Neutralization provided by the NEUTRIFF®.
c. % Increase = (Actual − Expected) ÷ (Expected). This is statistically significant $p < 0.05$.

EXAMPLE 2

NEUTRIFF® formulation described in Example 1 was added to the following fragrances in a ratio of 90:10 (Fragrance:NEUTRIFF®). The sensory evaluation technique and the calculation of the expected percent malodor neutralization are as described in the previous example.

NEUTRIFF® DATA

| Fragrance ID | % Pet Malodor Neutralization by Fragrance without NEUTRIFF® (a) | % Pet Malodor neutralization NEUTRIFF® Alone (a) | Expected % Pet Malodor Neutralization of Combination of Fragrance with NEUTRIFF® (b) | Actual % Pet Malodor Neutralization of Combination of Fragrance with NEUTRIFF® (a) | % Increase in Pet Malodor Neutralization (c) |
|---|---|---|---|---|---|
| B | 61 | 88 | 64 | 83 | 30 |
| C | 61 | 88 | 64 | 80 | 25 |
| D | 61 | 88 | 64 | 77 | 20 |
| E | 62 | 88 | 65 | 79 | 22 |
| F | 64 | 88 | 66 | 80 | 21 |
| G | 44 | 88 | 48 | 84 | 75 |
| H | 62 | 88 | 65 | 83 | 28 | a. % Neutralization = 100 × [1−malodor intensity/total intensity].
b. Expected % Neutralization = (concentration of original fragrance × % neutralization provided by the original fragrance) + (concentration of NEUTRIFF® × % Neutralization provided by the NEUTRIFF®.
c. % Increase = (Actual − Expected) ÷ (Expected). This is statistically significant $p < 0.05$.

Descriptions of Fragrances B–H are as follows:

| Fragrance | Description |
|---|---|
| B | Floral Fruity Woody Musk |
| C | Citrus Herbaceous |
| D | Citrus Herbaceous Fougere Fresh |
| E | Citrus Fruity Floral Woody Musk |
| F | Fruity Floral Woody Musk |
| G | Floral Amber Woody |
| H | Fresh Herbal Woody Mint |

CONCLUSION:

The original fragrances (A through H) as described in Examples 1 and 2, were developed to be aesthetically appropriate for a specific household product application. Although these fragrances are hedonically acceptable, they do not provide an adequate level of malodor neutralization. The NEUTRIFF® formulation described herein provides adequate malodor neutralization but lacks the aesthetic appeal, and variety, demonstrated by fragrances A through H. When the NEUTRIFF® is combined with any one of the example fragrances (A through H), an unexpected, unobvious and advantageous increase in malodor neutralization is achieved without significantly altering the hedonic impression. Furthermore, these combinations significantly improve the overall hedonics (of the test malodor) without significantly increasing the overall intensity.

The term GALAXOLIDE® is a mixture of compounds having the structures:

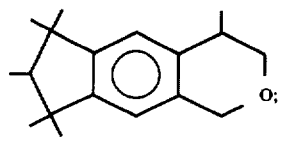

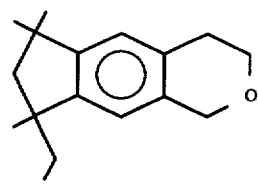

and

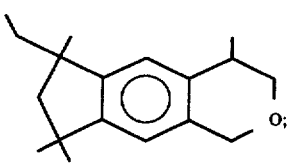

Other musks can be substituted for the GALAXOLIDE®, for example, those having the structures:

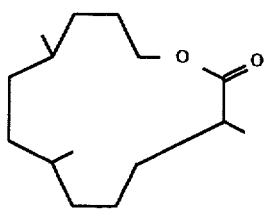

and

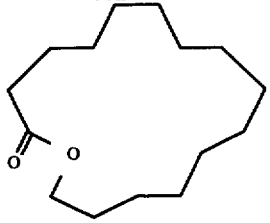

The citrus notes can be, for example, a mixture of 45–65% geranial having the structure:

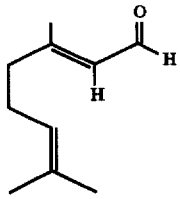

and 30–50% neral having the structure:

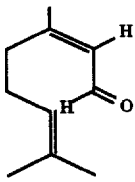

and such a mixture is also known as "citral".

What is claimed is:

1. A composition of matter consisting essentially of from about 20% up to about 60% of a musk aroma material which is GALAXOLIDE®, a mixture of compounds having the structures:

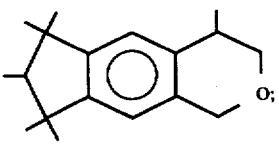

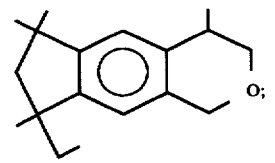

and

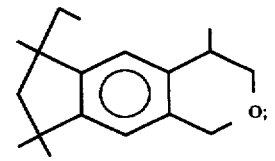

from about 30% up to about 70% by weight of a citrus aroma material which is CITRAL™, a mixture of compounds having the structures:

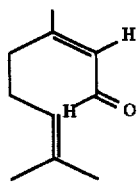

and from about 1% up to about 20% by weight of a mint aroma material which is corn mint oil as defined according to the spectra of FIGS. 1 and 2.

2. A process for neutralizing malodor which is selected from the group consisting of:

pet;

human urine;

human fecal;

smoking tobacco;

cooking;

garbage; and mildew comprising the steps of:

(1) admixing the composition of claim 1 with a compatible fragrance formulation whereby the weight percent of the composition of claim 8 in the final formulation is from about 0.5% up to about 20%; and (2) applying the resulting composition to a malodorous composition whereby the malodor thereof is neutralized.

3. A process for neutralizing malodor selected from the group consisting of:

pet;

human urine;

human fecal;

smoking tobacco;

cooking;

garbage; and mildew comprising the step of applying the composition of claim 1 to a malodorous composition whereby the malodor thereof is neutralized.

* * * * *

UNITED STATES PATENT AND TRADEMARK OFFICE
CERTIFICATE OF CORRECTION

PATENT NO. : 5,683,979
DATED : November 4, 1997
INVENTOR(S) : Lisa Schreck, et al.

It is certified that error appears in the above-identified patent and that said Letters Patent is hereby corrected as shown below:

Column 12,
Line 43, "claim 8" should be replaced with -- claim 1 --.

Signed and Sealed this

Second Day of October, 2001

Attest:

NICHOLAS P. GODICI
Attesting Officer    Acting Director of the United States Patent and Trademark Office